United States Patent [19]

Ohnishi

[11] Patent Number: 5,114,972

[45] Date of Patent: May 19, 1992

[54] SYNTHESIS AND USES OF NEW ASCORBIC ACID DERIVATIVES WHICH HAVE ANTI-OXIDANT AND ANTI-CANCER ACTIVITIES

[76] Inventor: Tsuyoshi Ohnishi, 502 King of Prussia Rd., Radnor, Pa. 19087

[21] Appl. No.: 559,480

[22] Filed: Jul. 30, 1990

[51] Int. Cl.$^5$ .......................................... C07C 177/00
[52] U.S. Cl. ..................................... 514/530; 560/121
[58] Field of Search ......................... 560/121; 514/530

[56] References Cited

U.S. PATENT DOCUMENTS 4,245,111 1/1981 Polis ................................. 514/530
4,389,414 6/1983 Kent ................................. 514/530

Primary Examiner—Robert Gerstl

[57] ABSTRACT

The invention is related to the novel compounds that have anti-oxident and anti-cancer activities. These compounds can protect (i) vital organs including the brain and the heart, (ii) skin cells, (iii) circulating cells such as red blood cells and white blood cells from physical, chemical and biological injuries either by pre-administration or post-administration. These compounds can be used to protect (iv) organs during transplant surgery by administering to a donar before removal of the organ and by administering to a receipient after transplantation. (v) These compounds can also protect red blood cells from the attack of malarial parasites. (vi) These compounds can be themselves be administered to cancer patients as low side-effect anti-cancer agents. They can also be administered to (vii) potentiate efficacy of existing other chemotherapeutic agents and (viii) to reduce side-effects of existing other chemotherapeutic agents. The compounds are synthesized by forming esters of ascorbic acid with either monomer of prostaglandin $B_2$ or oligomers of prostaglandin $B_2$. When compared with ascorbic acid in its original form, these esters have the following advantageous features: (a) they have high affinity to membrane lipids, thus they are more easily incorporated into cells; (b) they have a remarkable anti-oxidant activity; (c) these novel compounds can protect the cells and cell membranes by scavenging free radicals, which are known to deteriorate cell membranes; (d) these compounds possess anti-cancer activity; (e) they enhance the anti-cancer activity of existing other anti-cancer agents; and (f) they reduced the toxic side effects of other existing anti-cancer agents. These compounds can be administered orally, subcutaneously, intramuscularly, intravenously or topically.

6 Claims, 6 Drawing Sheets

SYNTHESIS AND USES OF NEW ASCORBIC ACID DERIVATIVES WHICH HAVE ANTI-OXIDANT AND ANTI-CANCER ACTIVITIES

BACKGROUND OF THE INVENTION

1. Field of the Invention

The present invention relates to new hydrophobic ascorbic ester compounds, which are synthesized by linking ascorbic acid either wit monomer prostaglandin $B_2$ or with oligomeric derivatives of prostaglandin $B_2$, as well as to methods of administering these compounds to protect organ cells, skin cells and circulating cells from various hypoxic, ischemic, physical, chemical or biological injuries. The invention also relates to methods of administering these compounds to cancer patients either as independent anti-cancer drugs or as supporting agents to enhance the efficacy of and to reduce the toxic side-effects of other commercially available anti-cancer agents.

2. Background Art

It has been theorized that ischemic, hypoxic, physical, chemical and biological injuries produce free radicals in the cells, which, in turn, attack proteins, membrane lipids and DNA to cause cell dysfunction and eventually cell death. By combining ascorbic acid and prostaglandin $B_2$, the inventor synthesized new hydrophobic ester compounds which can protect cells by scavenging these deleterious free radicals. The compounds were found to reduce toxic side-effects of currently used anti-cancer agents when administered simultaneously with these agents. It was found that these compounds not only enhanced the efficacy of currently used anti-cancer agents in this simultaneous administration, but also demonstrated anti-cancer activity by themselves.

SUMMARY OF THE INVENTION

It has been well-known that ascorbic acid (Vitamin C) is an important reducing agent in the cells. Since we humans live in the atmospheric air, and since we use oxygen to decompose nutrients to convert them to energy, our body cells are constantly exposed to oxidative stress. Under normal physiologic conditions, the cellular reducing power is greater than the oxidative stress, so that the toxic effect of oxygen is always negated. However, in ischemic or traumatic injury, this balance is overthrown. Since excess oxygen free radicals are produced upon ischemia or trauma, the oxidative stress exceeds the cellular reducing power, thereby oxidizing proteins, peroxidizing lipids, damaging DNA, and eventually leading the cells to death.

Although ascorbic acid is taken everyday through food or through supplemental vitamin pills, it has not been used as a drug for shock and trauma patients. We hypothesized that the high water solubility of ascorbic acid may result in low uptake to cellular membranes, thus limiting its use as a drug for treating emergency patients. In an attempt to synthesize strong anti-oxidant drugs with sufficient hydrophobicity, we developed novel compounds by forming an ascorbic acid ester of prostaglandin. The structure of the new compounds can be described as:

(AA-PG)$_n$ where AA stands for ascorbic acid and PG for prostaglandin $B_2$. The suffix n represents the number of monomer units in the oligomer, and it can be from 1 to 10.

The ester bond linking AA and PG was made between the OH group attached to the 6th carbon position of AA and the carboxyl group of PG. These compounds are abbreviated as OC-518n. We have tested monomer compounds OC-5181 and hexamer compounds OC-5186. It was found that these compounds have a strong anti-oxidant activity. In animal models, they protected cells from ischemic trauma. These compounds can be administered orally, subcutaneously, intramuscularly, intravenously or topically. They enter cells through the membranes, because these compounds have high affinity to lipids. Then, the compounds scavenge oxygen free radicals, thereby protecting the cells from ischemic or traumatic insult.

The inventor tested efficacy of these new compounds in various animal experiments as well as in in vitro experiments, which include (i) The inhibition of lipid peroxidation in ischemic rat brain.
(ii) The protection of the brain from ischemic damages.
(ii) The protection of the perfused rat heart from ischemic damage.
(iii) The protection of sickle red blood cells from sickling-unsickling damage.
(iv) The protection of red blood cells from infection by malarial parasites.
(v) The inhibition of tumor cell growth in mouse models.
(vi) The prolongation of the life-span of tumor-bearing mice.
(vii) The enhancement of the efficacy of 5-fluorouracil, a commercially used anti-cancer agent.
(viii) The reduction of the toxic-side effect of 5-fluorouracil.

FIGURE LEGENDS

FIG. 1. Inhibition of the rate of superoxide-induced adenochrome formation by OC-5186 (left panel) and by OC-5181 (right panel). The drugs were added at the positions indicated by arrows. The concentrations were 50 ug/ml each. The absorbance (A) was measured at 480 nm.

FIG. 2. Dose-response curves of free radical scavenging activity of OC-2186, 5181 and 5186.

FIG. 3. Dose-response relationship of TBAR inhibition by OC-2186 and 5186.

FIG. 4. Dose-response relationship of TBAR inhibition by a monomer, OC-5181.

FIG. 5. Effect of three compounds, OC-2186, 5181, and 5186 in an animal model. The concentrations of the drug were 9 mg/kg each.

FIG. 6. Spin adducts of hydroxyl radicals tapped by tert-butyl-(alpha)-phenylnitrone. (A) Hydroxyl radicals produced by 20 minutes of rat brain ischemia followed by 20 minutes recirculation. (B) Inhibition of the hydroxyl radicals by OC-5186 (9 mg/kg) injected I.P., 30 minutes prior to the ischemic insult.

DETAILED DESCRIPTION OF THE INVENTION

Figure 1:
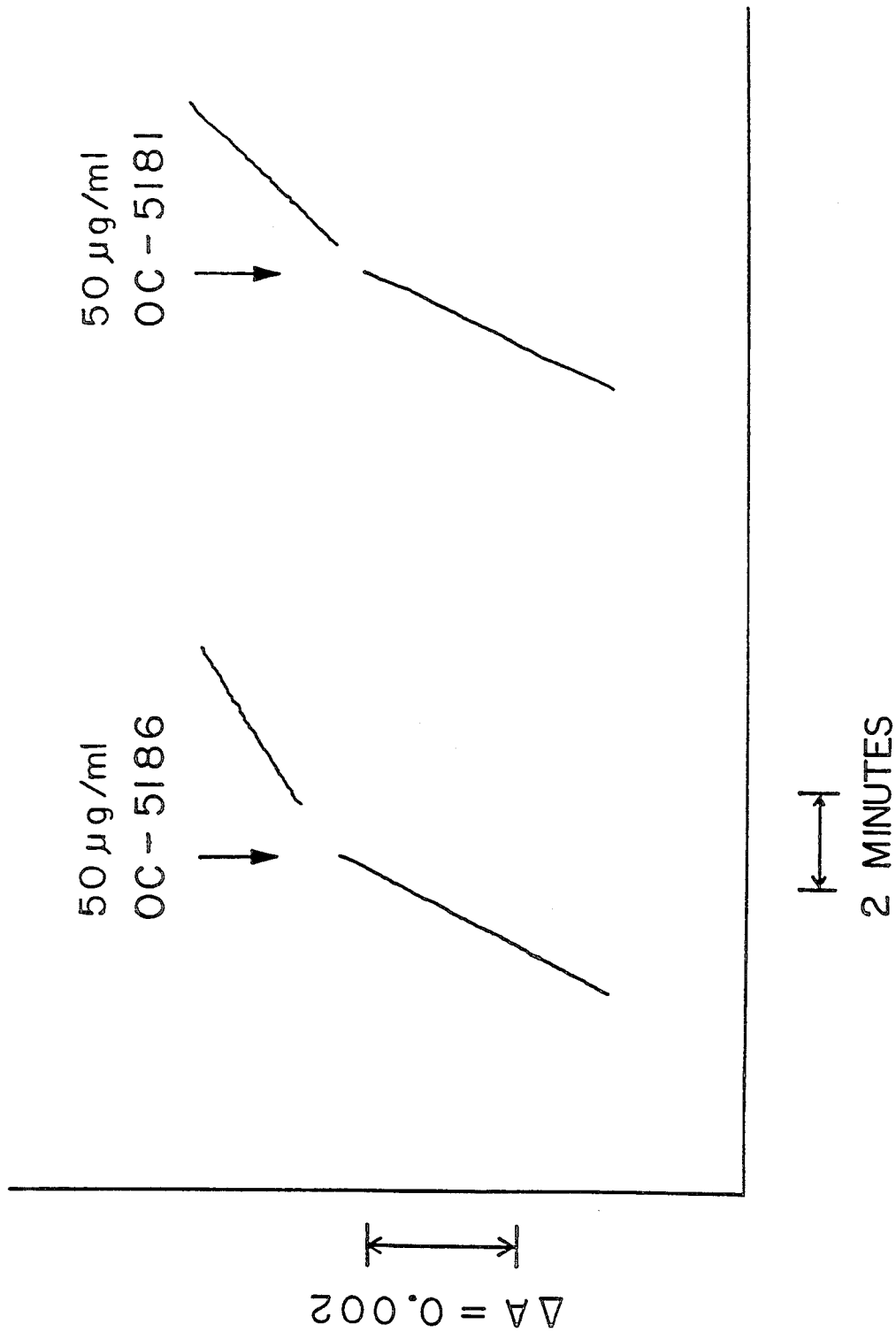

Examples of this invention are set forth below. However, it is to be understood that these examples are given by way of illustration only and are not to be construed as limiting the invention either in spirit or in scope, as many modifications both in reagents and methods could be possible to those skilled in the art. For example, instead of prostaglandin $B_2$, other compounds such as prostaglandin $A_2$, $E_2$, $A_1$, $B_1$ and $E_1$ can also be used.

Drug Preparation Method (a) A free-acid type prostaglandin oligomeric compound (which is called in this application as OC-2186) was synthesized from prostaglandin $B_2$ using a method similar to that developed by Polis and Polis, who prepared acid-form oligomers from prostaglandin $B_1$ (U.S. Pat. No. 4,153,808). In brief: 0.1 g of prostaglandin $B_2$ was dissolved in 10 ml ehtanol and added to 1.2 g crushed solid KOH in a 50 ml flask. The mixture was rotated on a reflux apparatus at 70° C. for three hours. Ten ml of water was added to make the final base concentration 1 N KOH in 50 % alcohol and the mixture was refluxed in an oil bath at 74° C. for an additional 6 hours. The reaction mixture was cooled to room temperature. 11 ml isobutanol was added and adjusted the pH to 3 with addition of about 7.5 ml 2.3 N $HClO_4$. The precipitate was removed by filtration. The precipitate was washed with an additional 10 ml of isobutanol. The filtrate and washing isobutanol solution were combined and washed twice with 10 ml of water and finally extracted with 25 ml of 0.1M $NaHCO_3$ freshly prepared (pH 8.5). 10 ml of isobutanol was added to the separated $NaHCO_3$ solution which contains oligomers, and the pH adjusted to 3 with 2.7 ml of 1 N HCl. The active components were then extracted into the isobutanol layer which was washed with $H_2O$, dried, and flash evaporated to yield a compound which is defined as OC-2186. This compound is in an acid form. The molecular weight of this compound as determined by vapor pressure osmometry was about 2,200 Daltons, suggesting that the major component of this compound may be hexamers, although dimer, trimer, tetramer, pentamer and heptamer may also be contained. The yield was 70-80%.

(b) Preparation of ascorbic acid ester with $PGB_2$ monomer or with OC-2186 was done as follows: We combined 1 g ascorbic acid and 0.5 g of either $PGB_2$ or $PGB_2$ oligomer in the presence of 6 ml pyridine, 1 g 1,3-dicyclohexylcarbodiimide, 0.2 g p-toluenesulfonic acid, and kept stirring for 12 hours at room temperature. After cooling the stirred materials to 0° C., 0.1 ml acetic acid was added to precipitate 1,3-dicyclohexylcarbodiimide. After filtering the mixture, the filtrate was evaporated in vacuo to produce a residue. The residue was dissolved in ethyl alcohol, and then a precipitate was produced by adding diethyl ether. The precipitate was separated from the supernatant containing p-toluenesulfonic acid by the centrifugation of 600×g for 5 minutes. We then dissolved the precipitate in isobutyl alcohol, and washed the solution with water to remove ascorbic acid. Finally we reevaporated the isobutyl alcohol layer, and extracting the residue with ethyl alcohol to produce the final product. The yield from the free acid compound was 80%. The molelcular weight of the comound was 3,000 Daltons. This ester-form is denoted as OC-5186 for an identification purpose. OC-5186 is not water soluble, but soluble in ethanol.

(c) Octanol-water partition ratio: The octanol-water partition ratio give an index of hydrophobicity of a compound. For example, if the ratio is one, a compound is equally soluble to water and octanol. In order to have high membrane affinity, a compound should have the ratio much higher than one. We found that the octanol-water partition ratio of OC-2186 and OC-5186 were 1.74 and 8.20, respectively. This result confirms that the ester-form compound is much more hydrophobic than the original acid-type prostaglandin oligomer.

(d) Toxicity: We injected I.P. a high dose of OC-5186 (60 mg/kg body weight) to five mice each. No toxicity was observed; the animals behaved normally.

Experimental Design and Results

EXAMPLE 1

Superoxide scavenging activity

Figure 2:
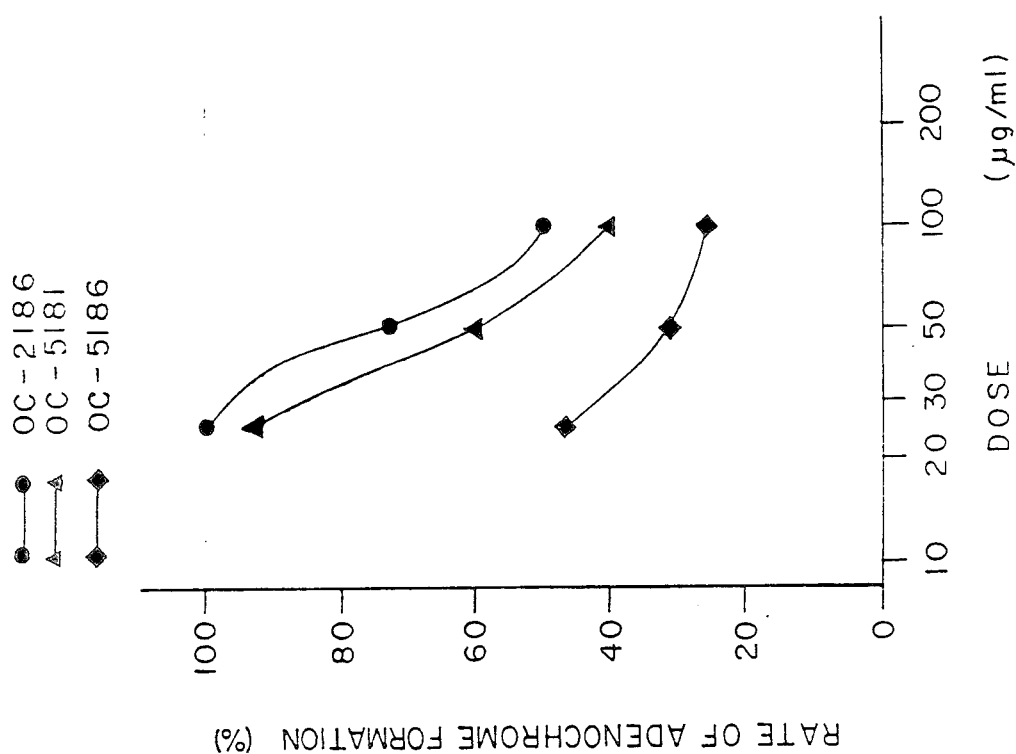

Using the adenochrome method (Misra and Fridovich, J. Biol. Chem. 247: 3170, 1972), we have measured the activity of these compounds to scavenge superoxide anions. FIG. 1 shows the superoxide-induced adenochrome formation. At the position indictated by arrows, OC-5186 or OC-5181 was added. Immediately the slope of the curve decreased, suggesting that superoxide production was reduced. From the change of the slope, we can estimate the activity of scavenging action. FIG. 2 shows the dose-response relationship of scavenging activity of three compounds. OC-5186 had the greatest antioxidant activity.

EXAMPLE 2

Figure 3:
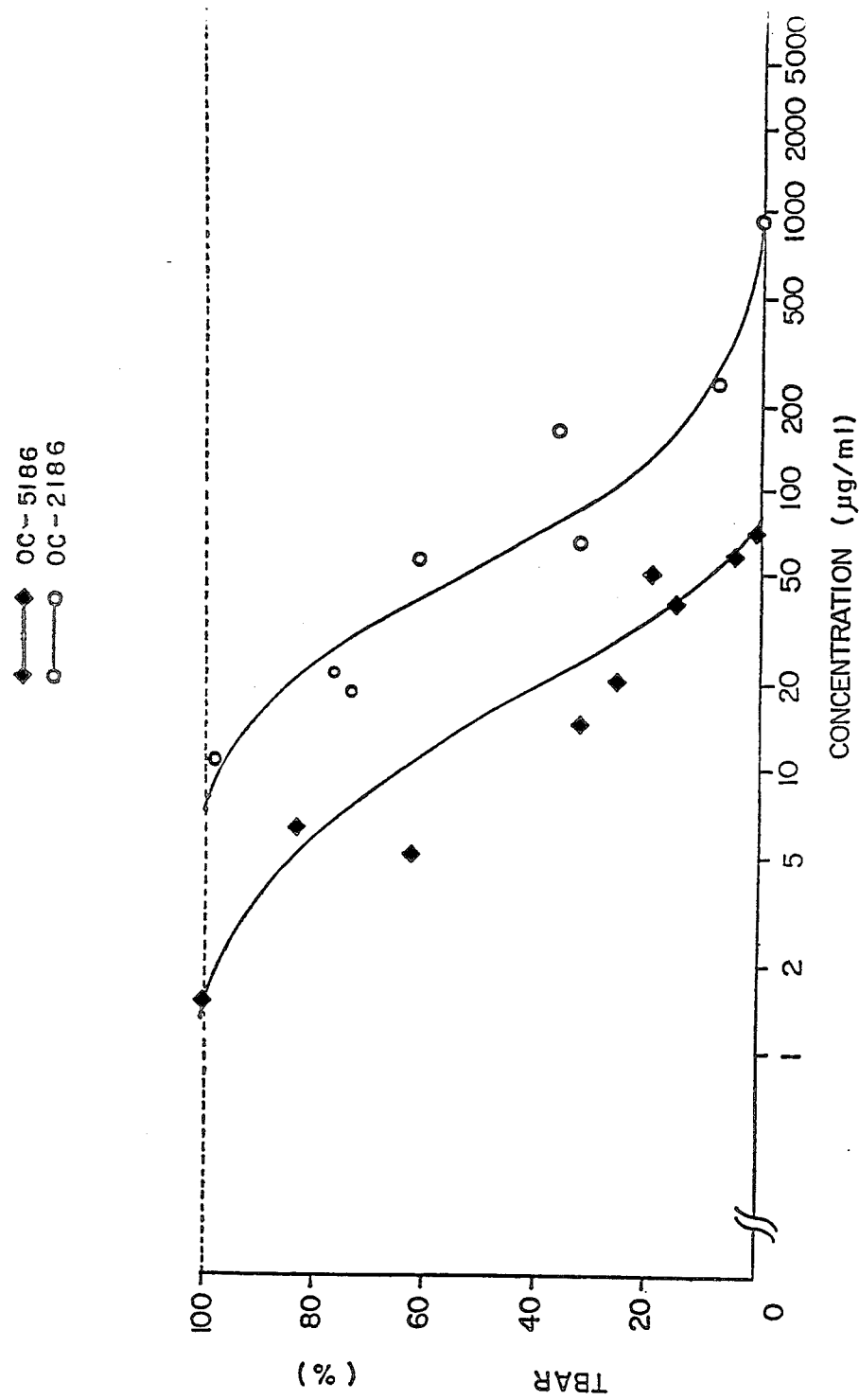
Figure 4:
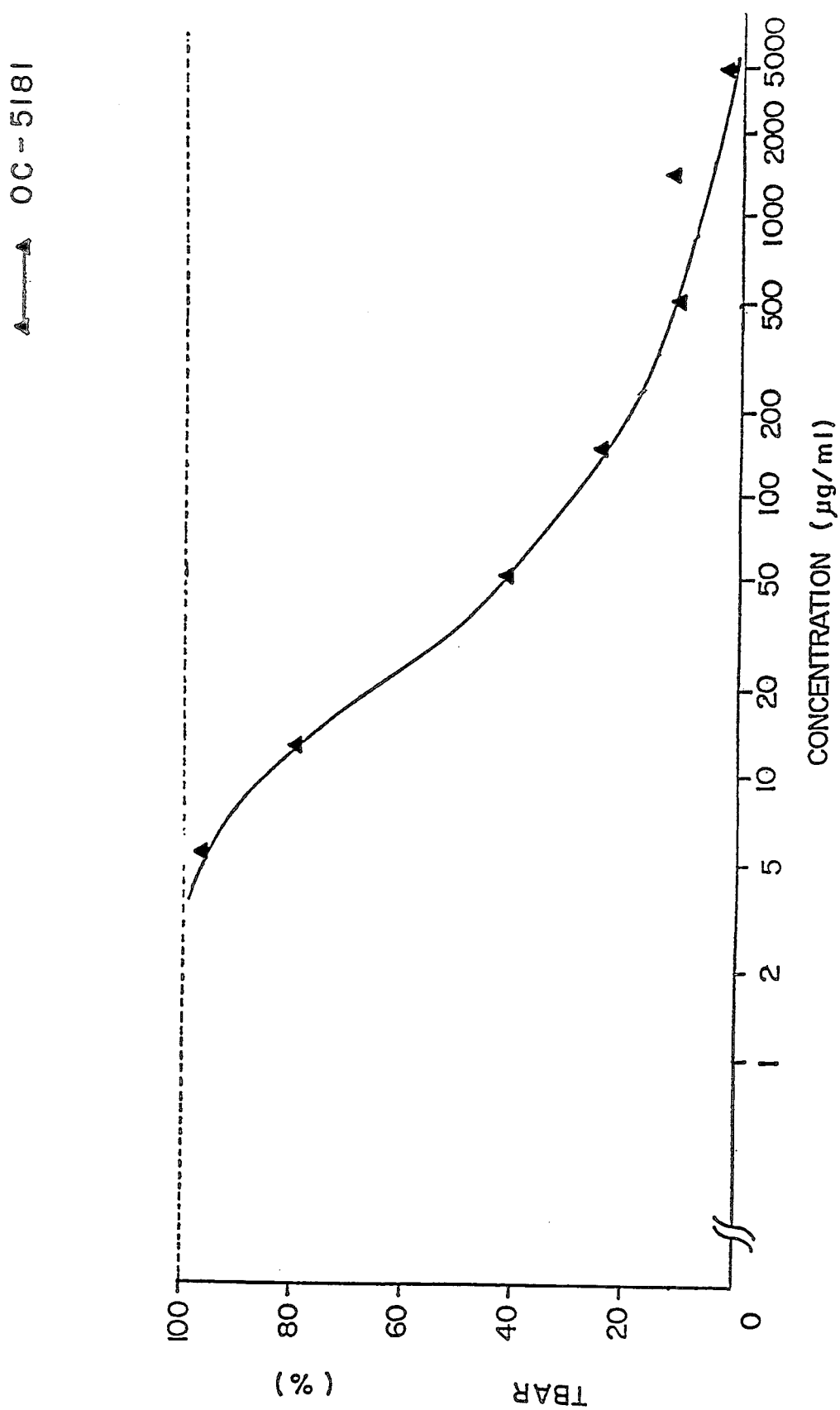

Protection of membranes (A) When cell membranes are exposed to ischemic or hypoxic insult, lipid peroxidation takes place. The degree of peroxidation can be measured by the production of thiobarbiturate reactive substances (TBAR). We have developed a simple assay method; we decapitate the rat and keep the head under a hypoxic condition for thirty minutes at 37 degrees and then homogenize it, then expose the homogenate to air for sixty minutes and measure the production of TBAR. FIG. 3 shows that TBAR production was inhibited by these compounds added in vitro before the exposure to air. Although OC-2186 had some antioxidant activity, OC-5186 had much greater antioxidant activity. FIG. 4 shows that monomer, OC-5181, had also antioxidant activity comparable to free acid type prostaglandin oligomers, OC-2186.

(B) An animal model experiment to determine the antioxidant activity of these compounds.

Figure 5:
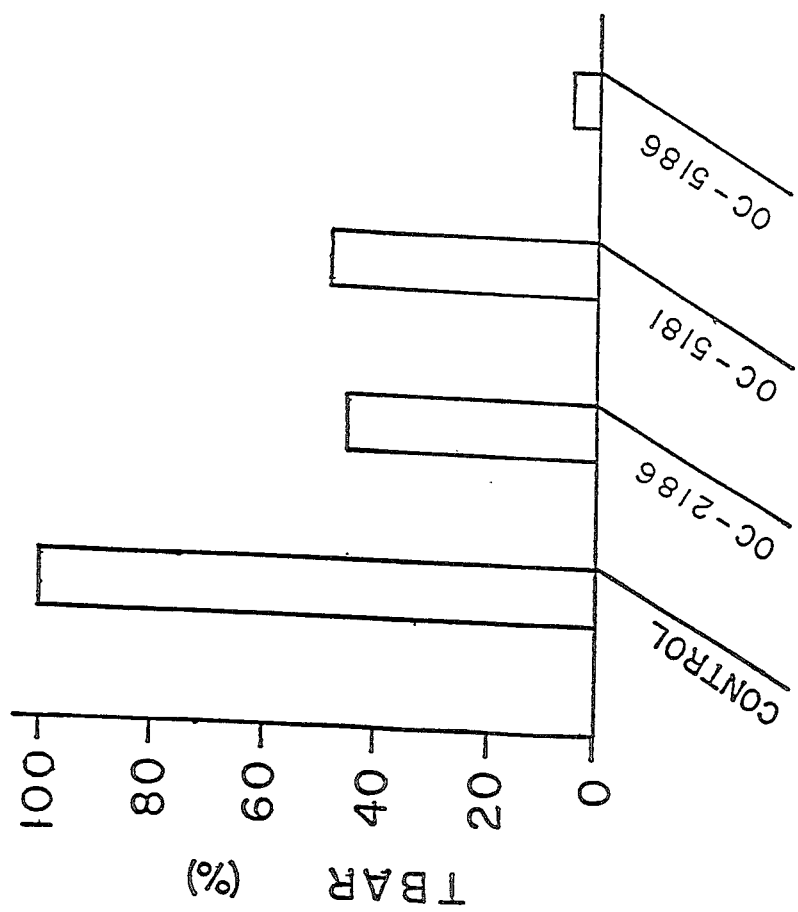

In this model, drugs were given to the rat via I.P. Thirty minutes later, the rat was decapitated to cause global brain ischemia. After keeping the head at 37 degrees for thirty minutes, the brain was removed, homogenated and the production of TBAR was measured. FIG. 5 shows such an experiment, where 9 mg/kg of different compounds were injected I.P thirty minutes before decapitation. Drugs given in vivo inhibited the amount of TBAR production. OC-5186 had the greatest activity.

EXAMPLE 3

Protective effect of drugs on brain ischemia

Figure 6:
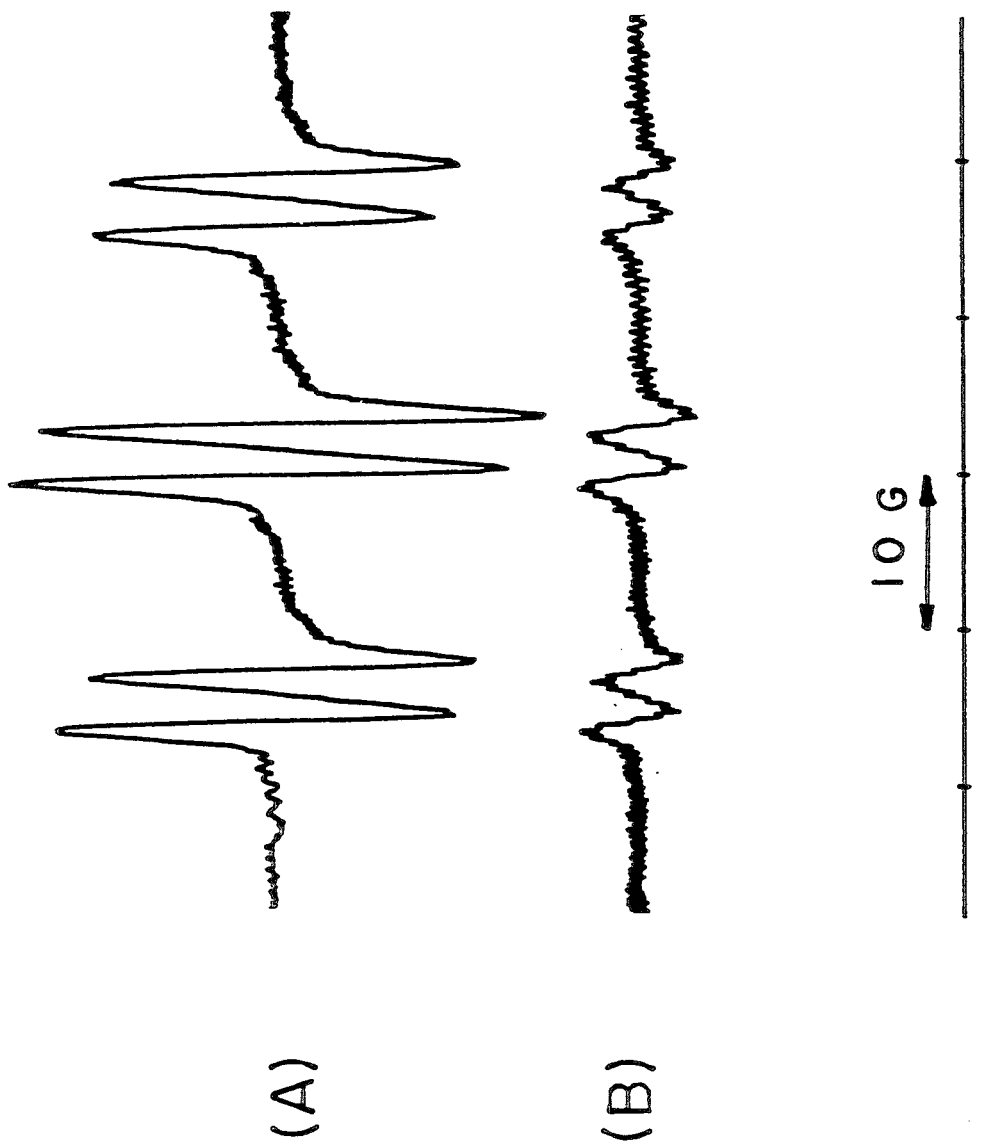

Adult, male Sprague-Dawley rats, weighing 300 to 350 grams, were used to prepare global ischemia. Anesthesia was induced and maintained with forane in 70% nitrous oxide-30% oxygen. After trachea was intubated, anesthesia was maintained using a ventilator. Both common carotid arteries were exposed and occluded by microaneurysmal clips. Then 12 to 14 ml of blood was withdrawn from the tail vein to bring the blood pressure to 30 mm Hg, which caused global ischemia. After twenty minutes of ischemia, blood was reinfused, clips were removed to induce recirculation. After twenty minutes of recirculation, the rat was decapitated, the brain was removed in ice-cold saline and then homogenized for TBAR measurement and spin trap measurement. For the measurement of survival rate, the wound was sutured and the animal recovered. The animal was returned to its cage. They were then observed for the survival rate. FIG. 6 shows the measurement of hydroxyl radical produced by ischemia-recirculation injury. FIG. 6(A) shows that the hydroxyl radical produced by ischemia. In this experiment, the brain was homogenized in the presence of 50 mM tert-butyl-(alpha)-phenylnitrone and the homogenate was introduced to electron spin resonance spectrophotometer. The result clearly demonstrated the production of hydroxyl radicals after twenty minutes of ischemia and twenty minutes recirculation. FIG. 6(B) demonstrates that the production was greatly suppressed if OC-5186 (9 mg/kg) was injected I.P. thirty minutes prior to the ischemic insult.

OC-5186 remarkably improved the survival rate after ischemia. In control experiment, where no drug was introduced, 8 out of 8 animals died within 2 days. However, when 9 mg/kg OC-5186 was injected I.P. thirty minutes prior to ischemia, four out of four survived. Ascorbic acid (9 mg/kg) had no effect.

EXAMPLE 5

Protection of isolated perfused rat heart

These drugs were found to protect the isolated beating heart (Langendorff model) from ischemia. In this experiment, an isolated rat heart was mounted by tieing the aorta to a catheter. Then a modified Krebs-Henseleit solution (117 mM NaCl, 6 mM KCl, 2.5 mM $CaCl_2$, 1.2 mM $MgCl_2$, 2.4 mM phosphate, 24 mM $NaHCO_3$, 5 mM glucose; bubbled with 95% $O_2$-5% $CO_2$ gas; temperature 37°; pH 7.4) was circulated by a pump (flow rate: 15 ml/min). The heart was stimulated 3 beats/seconds by electric pulses(10 V; 10 m sec duration). This system supported the beating heart for more than several hours. The left ventricular developed pressure was measured by inserting a catheter with a small latex balloon attached at the tip, and by connecting the catheter to a Statham pressure transducer P23Gb After equilibration, the flow of Krebs-Hensleit solution was stopped for 20 minutes. If no drug was added, the heart did not recover after the flow was restarted. However, if 50 ug/ml OC-5186 was added to the perfusate before restarting the flow, the left ventricular developed pressure recovered more than 80 %. Thus, the drug was able to protect the heart from the reperfusion injury.

EXAMPLE 6

Sickle cell anemia

The inventor previously developed the method to produce irreversibly sickled cells (ISC, which are irreversibly denatured sickle cells) by exposing sickle red blood cells to a repeated sickling-unsickling cycling in vitro. He used this system to determine the efficacy of drugs in protecting cell membranes (Ohnishi, Br. J. Haematol. 55:665-671, 1983; Ohnishi et al. Biochim. Biophys. Acta 886:119-129, 1986). When sickle cells were exposed to a sickling-unsickling cycling for 3 hours, about half of the cells were denatured as revealed by the formation of heavy, dehydrated cells in density gradient centrifugation. These heavy cells were collected, the amount measured, and the percentage of production calculated. When 10 ug/ml of OC-5186 was added, the formation of irreversibly denatured cells was inhibited by 80%. Ascorbic acid (10 ug/ml) did not inhibit the formation.

EXAMPLE 7

Malaria

The FCR-3 strain *P. falciparum* was used. Blood-stage parasites were cultured in RPMI-1640 (GIBCO Laboratories, Chagrin Falls, Ohio) in 96 well flat bottomed plates (Costar; Cambridge, Mass.) using the candle jar method described by Jensen and Trager (J. Parasitology 63:883,1977) and modified by Grun and Weidanz (J. Parasitology 73:384, 1987). Parasitemia was estimated on GIEMSA stained films of cultures. For drug administration, desired amounts of chemicals were added to an individual wells of 96 well plates. Forty-eight hours later, parasitemia was estimated and the degree of growth inhibition was determined. When 25 ug/ml of OC-5186 was added, the growth of *P. falciparum* in in vitro culture was inhibited by 50%. When 50 ug/ml was added, it completely inhibited the growth. Ascorbic acid (50 ug/ml) did not inhibit the growth.

EXAMPLE 7

Cancer Study

(A) Anti-cancer activity

We used two mice models (Tomomatsu, Morita, Nagai, Shiwaku, Ichiki and Yonoki: Acta Med. Univ. Kagoshima. 17:99, 1975), i.e., (a) Ehrlich's ascites tumor (EAT) model and (b) a solid tumor model in which EAT cells were innoculated subcutaneously. In (a), $10^7$ tumor cells were injected I.P. in a mouse with the body weight of 20 g. In (b), the same amount of tumor cells were injected subcutaneously in a mouse of similar weight. After 21 days, we measured several parameters: (i) the change of body weight; (ii) average time to their death, from which we measure extension of life span, and (iii) survival rate.

In the ascites tumor model, an increase of body weight is related to the increase in ascites. When the animal dies, we collect the ascites fluid and measure the number of tumor cells found in the ascites.

In the solid tumor model, we measured the extension of the life span and the survival rate. When the animal died, we measured the weight of the solid tumor (Table 1 shows such data). In the Experiment 1, from day 4 until day 13 (for ten days), anti-cancer drugs were administered. We used OC-5186 at the dose of 10 mg/kg/day and 5-fluorouracil (5-FU: a widely used anti-cancer agent) at the dose of 20 mg/kg/day. In the combination therapy, both drugs were administered simultaneously at their respective doses. In the EAT model, control animals died in an average of 17 days, whereas animals with OC-5186 (10 mg/kg/day) died in an average of 19.7 days. With the 5-FU, they died in an average of 20.3 days. The survival rate of control mice was 25%, that for OC-5186 was 33.3% and that for 5-FU was 40%. When animals were treated with both OC-5186 and 5-FU, the average life span was extended to 20.8 days and the survival rate was improved to 75% (Table 1 (a)). In the tumor model, similar tendency was observed. It is also noted that the growth of solid tumor was also suppressed with this regimens (Table 1 (b)).

In the Experiment 2, the amount of the oligomer was cut down to 1 mg/kg/day to see whether we could still observe anti-cancer activity. OC-5186 and/or 5-FU (20 mg/kg/day) were administered for 23 days. Even at this low dose, OC-5186 still demonstrated its efficacy. Especially in the combined therapy (OC-5186 plus 5-FU), the average life span in model (a) was extended to 25.5 days and the survival rate was again improved to 50% (Table 2 (a)). In model (b), the combination therapy was also effective (Table 2 (b)). (B) Reduction of toxic side-effect of 5-FU by OC-5186.

It should be emphasized that in the combination therapy in Experiment 2, both OC-5186 and 5-FU were administered for 23 days, but most of animals survived the chemotherapy. Without OC-5186, 5-FU can not be administered for longer than 10 days; because of the toxicity of 5-FU, all animals die if it is administered for 23 days.

TABLE 1

Results of Experiment 1 on (a) Ehrlich's ascites tumor (EAT) model and (b) Solid tumor-model

|  | (a)EAT model | | (b) Solid tumor model |
|---|---|---|---|
|  | Average survival | 21 day survival | Solid tumor weight (on 21 days) |
| Control | 17.0 days | 25% | 1.2 g |
| OC-5186 (10 mg/kg/day) | 19.7 | 33.3 | 1.0 |
| 5-FU (20 mg/kg/day) | 20.3 | 40 | 0.70 |
| OC-5186 and 5-FU | 20.8 | 75 | 0.31 |

TABLE 2

Results of Experiment 2 on (a) Ehrlich's ascites tumor (EAT) model and (b) Solid tumor model

|  | (a)EAT model | | (b) Solid tumor model | |
|---|---|---|---|---|
|  | Average survival | 21 day survival | Av. Surv. | 21 day surv. |
| Control | 15.3 days | 0% | 23.2 days | 25% |
| OC-5186 (1 mg/kg/day) | 17.0 | 0 | 23.9 | 30 |
| 5-FU (20 mg/kg/day) | 20.3 | 40 | 26 | 40 |
| OC-5186 and 5-FU | 25.5 | 50 | 30.5 | 75 |

I claim:

1. A preparation method for synthesizing ascorbic acid 6-prostaglandin esters; said method comprising forming ester compounds of ascorbic acid either with prostaglandin B$_2$ monomer (PGB$_2$) or with its oligomer, which is prepared from the monomer PGB$_2$ by the alkaline polymerization method; said preparation method further comprising combining 1 g ascorbic acid and 0.5 g of either PGB$_2$ or PGB$_2$ oligomer in the presence of 6 ml pyridine, 1 g 1,3-dicyclohexylcarbodiimide, 0.2 g p-toluenesulfonic acid, stirring for 12 hours at room temperature, cooling said stirred materials to 0° C., adding 0.1 ml acetic acid to produce a precipitate of 1,3-dicyclohexylcarbodiimide, producing a filtrate by filtering the said precipitate, evaporating said filtrate in vacuo to produce a residue, taking up the residue in ethyl alcohol, producing a precipitate by adding diethyl ether to said ethyl alcohol solution, separating the said precipitate from the supernatant containing p-toluenesulfonic acid by the centrifugation of 600×g for 5 minutes, dissolving the said precipitate in isobutyl alcohol, washing the said solution with water to remove ascorbic acid, reevaporating the isobutyl alcohol layer, and extracting the residue with ethyl alcohol.

2. Methods of protecting the brain and the heart against ischemic injury by administering the ester-compounds of claim 1 either pre-injury or post-injury at a dosage of
  (a) orally at least 20 mg/kg body weight/day or
  (b) subcutaneously or intramuscularly at least 9 mg/k body weight/day or
  (c) intravenously at least 6 mg/kg body weight/day.

3. The method of protecting organs from deterioration during organ transplant surgery by administering the ester-compounds of claim 1, to the donor prior to the organ removal at any one of the dosages given in claim 2, and by administering these compounds to the recipient after the organ transplant at dosages given in claim 2.

4. The method of protecting blood cells by administering compounds of claim 1 at any one of the dosages given in claim 2.

5. The method of claim 4 involving protecting red blood cells of sickle cell anemia patients by administering compounds of claim 1 at any one of the dosages in claim 2.

6. The method of claim 4 involving protecting red blood cells from the attack of malarial parasites by administering compounds of claim 1 at any one of the dosages in claim 2.

* * * * *